United States Patent
Wan et al.

(10) Patent No.: US 11,925,756 B2
(45) Date of Patent: Mar. 12, 2024

(54) ANESTHESIA MACHINE, ANESTHETIC OUTPUT CONCENTRATION MONITORING METHOD, SYSTEM, AND DEVICE, AND STORAGE MEDIUM

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Congying Wan, Shenzhen (CN); Xiaoyong Zhou, Shenzhen (CN); Peitao Chen, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 1004 days.

(21) Appl. No.: 16/847,640

(22) Filed: Apr. 13, 2020

(65) Prior Publication Data
US 2020/0238033 A1 Jul. 30, 2020

Related U.S. Application Data

(63) Continuation of application No. PCT/CN2017/107997, filed on Oct. 27, 2017.

(51) Int. Cl.
*A61M 16/00* (2006.01)
*A61M 16/01* (2006.01)
(Continued)

(52) U.S. Cl.
CPC .......... *A61M 16/024* (2017.08); *A61M 16/01* (2013.01); *A61M 16/22* (2013.01);
(Continued)

(58) Field of Classification Search
CPC .............. A61M 16/024; A61M 16/026; A61M 16/022; A61M 16/021; A61M 16/01;
(Continued)

(56) References Cited

U.S. PATENT DOCUMENTS

| 4,903,693 A * | 2/1990 | Yasue | A61M 16/085 |
| | | | 600/541 |
| 6,216,690 B1 * | 4/2001 | Keitel | A61M 16/026 |
| | | | 128/204.21 |

(Continued)

FOREIGN PATENT DOCUMENTS

| CN | 101231186 A | 7/2008 |
| CN | 102264292 A | 11/2011 |

(Continued)

OTHER PUBLICATIONS

First Office Action issued in related Chinese Application No. 201780095449.2, dated Jul. 22, 2022, 6 pages.

(Continued)

*Primary Examiner* — Joseph D. Boecker
*Assistant Examiner* — Brian T Khong
(74) *Attorney, Agent, or Firm* — BAYES PLLC

(57) ABSTRACT

An anesthesia machine, an anesthetic output concentration monitoring method, system, a device, and a storage medium are disclosed. The method includes respectively monitoring a flow of a fresh gas flowing into a breathing circuit and a flow of an inhaled gas of an anesthetized object. The method further includes when the inhaled gas flow is greater than a fresh gas flow, respectively monitoring a concentration of anesthetic in the inhaled gas and an exhaled gas of the anesthetized object. The method also includes using the exhaled gas anesthetic concentration and a concentration of carbon dioxide in the exhaled gas to calculate a concentration of anesthetic in a gas, reflowing into an inspiratory (Continued)

branch, in the exhaled gas, thereby obtaining a re-inhaled gas anesthetic concentration. The method additionally includes using the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration.

20 Claims, 5 Drawing Sheets

(51) Int. Cl.
*A61M 16/22* (2006.01)
*G16H 40/60* (2018.01)

(52) U.S. Cl.
CPC ..... *G16H 40/60* (2018.01); *A61M 2016/0018* (2013.01); *A61M 2016/0039* (2013.01); *A61M 2230/437* (2013.01)

(58) Field of Classification Search
CPC ............ A61M 16/0045; A61M 16/009; A61M 16/0891; A61M 16/0883; A61M 16/104; A61M 2016/003; A61M 2016/0033; A61M 2016/0036; A61M 2016/0039; A61M 2016/0042; A61M 2016/103; A61M 2016/1035
See application file for complete search history.

(56) References Cited

U.S. PATENT DOCUMENTS

| | | | |
|---|---|---|---|
| 2007/0173729 A1* | 7/2007 | Fisher | A61M 16/206 128/203.14 |
| 2008/0029092 A1* | 2/2008 | Heesch | A61M 16/01 128/203.14 |
| 2009/0090359 A1* | 4/2009 | Daviet | A61M 16/104 128/203.14 |
| 2010/0101571 A1* | 4/2010 | Messerges | A61M 16/104 128/203.14 |
| 2011/0105934 A1* | 5/2011 | Blandin | A61M 16/12 600/532 |
| 2012/0031402 A1* | 2/2012 | Loncar | A61M 16/18 128/203.14 |
| 2012/0291784 A1 | 11/2012 | Robinson et al. | |
| 2015/0059744 A1* | 3/2015 | Fisher | A61M 16/024 128/203.14 |
| 2015/0144135 A1 | 5/2015 | Heinonen | |
| 2016/0213867 A1 | 7/2016 | Robinson et al. | |
| 2018/0093063 A1* | 4/2018 | Rajan | A61M 16/0066 |

FOREIGN PATENT DOCUMENTS

| | | |
|---|---|---|
| CN | 102688546 A | 9/2012 |
| CN | 102695538 A | 9/2012 |
| CN | 105031792 A | 11/2015 |
| CN | 105879177 A | 8/2016 |
| IN | 107050605 A | 8/2017 |
| JP | 2001095921 A | 4/2001 |
| JP | 2004041247 A | 2/2004 |
| WO | 03/082390 A1 | 10/2003 |
| WO | 2010/081914 A1 | 7/2010 |
| WO | 2017137055 A2 | 8/2017 |

OTHER PUBLICATIONS

Extended European Search Report issued in related European Application No. 17930047.0, dated Mar. 31, 2021, 8 pages.
International Search Report issued in corresponding International Application No. PCT/CN2017/107997, dated Aug. 9, 2018, 4 pages.
Communication pursuant to Article 94(3) EPC issued in related European Application No. 17930047.0, dated Jun. 30, 2023, 9 pages.

* cited by examiner

ANESTHESIA MACHINE, ANESTHETIC OUTPUT CONCENTRATION MONITORING METHOD, SYSTEM, AND DEVICE, AND STORAGE MEDIUM

CROSS-REFERENCE TO RELATED APPLICATIONS

This application is a bypass continuation of PCT App. No. PCT/CN2017/107997, filed Oct. 27, 2017, for ANESTHESIA MACHINE, ANESTHETIC OUTPUT CONCENTRATION MONITORING METHOD, SYSTEM, AND DEVICE, AND STORAGE MEDIUM, which is incorporated herein in its entirety by reference.

TECHNICAL FIELD

The present disclosure relates to the technical field of anesthesia machines, and in particular to an anesthesia machine, an anesthetic output concentration monitoring method, system, and device, and a storage medium.

BACKGROUND

An anesthesia machine delivers anesthetic gas to a breathing circuit of a patient by means of an evaporator to achieve the purpose of performing anesthesia for a patient. At present, most mid- and low-end anesthesia machines are not equipped with a gas module that may monitor an anesthetic output concentration of an evaporator, but only monitor, at a patient end, an inhaled gas anesthetic concentration and an exhaled gas anesthetic concentration of the patient. Due to the lack of a measure of monitoring the anesthetic output concentration of the evaporator, mid- and low-end anesthesia machines have the following problems. When an evaporator fails, the failure may only be detected through the abnormal inhaled gas anesthetic concentration and exhaled gas anesthetic concentration of the patient. Because an anesthesia machine has a relatively large circuit volume, there may be a very long delay before the failure is detected. In addition, it is difficult to calculate the consumption of anesthetic, which affects the accuracy of charges for surgery given that the consumption of anesthetic is an important basis for charges for surgery in many hospitals.

In order to resolve these problems, some anesthesia machines are additionally provided with a monitoring device configured to monitor the concentration of gas at an outlet of an evaporator. This solution will increase the cost and thus is not applicable to mid- and low-end anesthesia machines.

In addition, some manufacturers add, at a patient end, with a gating air path through which gas is sampled at a rear end of the evaporator at regular intervals, and then perform concentration analysis on the sampled gas, thereby obtaining an anesthetic output concentration of the evaporator. This solution relies on an additional device that supports time-sharing sampling, resulting in increased costs.

In summary, it may be seen that the problem to be solved at present is how to achieve the purpose of monitoring an anesthetic output concentration based on the premise of low costs.

SUMMARY

In view of this, an objective of the present disclosure is to provide an anesthesia machine, an anesthetic output concentration monitoring method, system, and device, and a storage medium, so that an anesthetic output concentration may be monitored at low costs. Specific solutions of the present disclosure are as follows:

According to a first aspect, the present disclosure discloses an anesthetic output concentration monitoring method, including:

respectively monitoring a flow of a fresh gas flowing into a breathing circuit and a flow of an inhaled gas of an anesthetized object, thereby correspondingly obtaining a fresh gas flow and an inhaled gas flow;

when the inhaled gas flow is greater than the fresh gas flow, respectively monitoring a concentration of anesthetic in the inhaled gas and an exhaled gas of the anesthetized object, thereby correspondingly obtaining an inhaled gas anesthetic concentration and an exhaled gas anesthetic concentration;

using the exhaled gas anesthetic concentration and a concentration of carbon dioxide in the exhaled gas to calculate a concentration of anesthetic in a gas, reflowing into an inspiratory branch, in the exhaled gas, thereby obtaining a re-inhaled gas anesthetic concentration; and using the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration.

Optionally, the step of using the exhaled gas anesthetic concentration and a concentration of carbon dioxide in the exhaled gas to calculate a concentration of anesthetic in a gas, reflowing into an inspiratory branch, in the exhaled gas, thereby obtaining a re-inhaled gas anesthetic concentration includes:

using the exhaled gas anesthetic concentration, the concentration of carbon dioxide in the exhaled gas, and a calculation model for the re-inhaled gas anesthetic concentration to calculate the concentration of anesthetic in the gas, reflowing into the inspiratory branch, in the exhaled gas, thereby obtaining the re-inhaled gas anesthetic concentration;

wherein the calculation model for the re-inhaled gas anesthetic concentration is a model created based on a process of changes in an anesthetic concentration caused by a carbon dioxide absorption canister.

Optionally, the step of using the exhaled gas anesthetic concentration and a concentration of carbon dioxide in the exhaled gas to calculate a concentration of anesthetic in a gas, reflowing into an inspiratory branch, in the exhaled gas, thereby obtaining a re-inhaled gas anesthetic concentration includes:

using the exhaled gas anesthetic concentration, the concentration of carbon dioxide in the exhaled gas, and an analysis result of changes in an anesthetic concentration to calculate the concentration of anesthetic in the gas, reflowing into the inspiratory branch, in the exhaled gas, thereby obtaining the re-inhaled gas anesthetic concentration;

wherein the analysis result of changes in the anesthetic concentration is a result obtained after an analysis of a process of changes in an anesthetic concentration in a reflowing branch, and the reflowing branch is provided with an exhaled gas branch, a re-inhaled gas buffer device, and a carbon dioxide absorption canister.

Optionally, the step of obtaining the analysis result of changes in the anesthetic concentration includes:

analyzing the process of changes in the anesthetic concentration in the reflowing branch by means of a delayer and a filter, thereby obtaining the analysis result of changes in the anesthetic concentration.

Optionally, the step of obtaining the analysis result of changes in the anesthetic concentration includes:

respectively creating corresponding models for the exhaled gas branch, the re-inhaled gas buffer device, and the carbon dioxide absorption canister based on a predetermined gas delivery model that is used to characterize a relationship between an inflow gas anesthetic concentration and an outflow gas anesthetic concentration of an analysis object, thereby obtaining an anesthetic concentration analysis result including a first gas delivery model, a second gas delivery model, and a third gas delivery model.

Optionally, before the step of using the exhaled gas anesthetic concentration and a concentration of carbon dioxide in the exhaled gas to calculate a concentration of anesthetic in a gas, reflowing into an inspiratory branch, in the exhaled gas, further includes:

determining a calculation precision requirement of the re-inhaled gas anesthetic concentration; and determining a corresponding re-inhaled gas anesthetic concentration calculation method according to the calculation precision requirement of the re-inhaled gas anesthetic concentration.

Optionally, the step of determining the calculation precision requirement of the re-inhaled gas anesthetic concentration includes:

obtaining a branch parameters of a reflowing branch, wherein the branch parameters of the reflowing branch include a length or a volume of the reflowing branch or a flow of gas flowing from the reflowing branch to the inspiratory branch; and determining the calculation precision requirement of the re-inhaled gas anesthetic concentration according to the branch parameters of the reflowing branch.

Optionally, after the step of respectively monitoring a flow of a fresh gas flowing into a breathing circuit and a flow of an inhaled gas of an anesthetized object, thereby correspondingly obtaining a fresh gas flow and an inhaled gas flow, the method further includes:

when the inhaled gas flow is less than or equal to the fresh gas flow, monitoring a concentration of anesthetic in the inhaled gas of the anesthetized object, and directly determining the concentration of anesthetic as the concentration of output anesthetic of the anesthetic output device.

Optionally, the anesthetic output concentration monitoring method further includes:

determining whether the anesthetic output concentration is greater than a preset output concentration threshold, and if yes, triggering a corresponding abnormal response operation.

Optionally, the anesthetic output concentration monitoring method further includes:

using the anesthetic output concentration and the fresh gas flow to calculate and display an anesthetic consumption rate or an anesthetic consumption amount in the anesthetic output device.

Optionally, the step of using the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration includes:

using the fresh gas flow, the inhaled gas flow, the inhaled gas anesthetic concentration, the re-inhaled gas anesthetic concentration, and a first output concentration calculation model to calculate the concentration of output anesthetic of the anesthetic output device, thereby correspondingly obtaining the anesthetic output concentration;

wherein the first output concentration calculation model is a model created based on the premise that a process of changes in an anesthetic concentration in the inspiratory branch is ignored.

Optionally, the step of using the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration includes:

using the fresh gas flow, the inhaled gas flow, the inhaled gas anesthetic concentration, the re-inhaled gas anesthetic concentration, a predetermined change rate for the inhaled gas anesthetic concentration, and a second output concentration calculation model to calculate the concentration of output anesthetic of the anesthetic output device, thereby correspondingly obtaining the anesthetic output concentration;

wherein the second output concentration calculation model is a model created based on the premise that a process of changes in an anesthetic concentration in the inspiratory branch is considered.

According to a second aspect, the present disclosure discloses an anesthetic output concentration monitoring system, including:

a flow monitoring module configured to respectively monitor a flow of a fresh gas flowing into a breathing circuit and a flow of an inhaled gas of an anesthetized object, thereby correspondingly obtaining a fresh gas flow and an inhaled gas flow;

a concentration monitoring module configured to, when the inhaled gas flow is greater than the fresh gas flow, respectively monitor a concentration of anesthetic in the inhaled gas and an exhaled gas of the anesthetized object, thereby correspondingly obtaining an inhaled gas anesthetic concentration and an exhaled gas anesthetic concentration;

a re-inhaled gas anesthetic concentration calculation module configured to use the exhaled gas anesthetic concentration and a concentration of carbon dioxide in the exhaled gas to calculate a concentration of anesthetic in a gas, reflowing into an inspiratory branch, in the exhaled gas, thereby obtaining a re-inhaled gas anesthetic concentration; and an anesthetic output concentration calculation module configured to use the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration.

According to a third aspect, the present disclosure discloses an anesthetic output concentration monitoring device, including a first flow sensor, a second flow sensor, an anesthetic concentration sensor, a processor, and a memory, wherein the processor is configured to execute a computer program stored in the memory to implement the following steps:

monitoring a flow of fresh gas flowing into a breathing circuit based on the first flow sensor, thereby correspondingly obtaining a fresh gas flow;

monitoring a flow of inhaled gas of an anesthetized object based on the second flow sensor, thereby correspondingly obtaining an inhaled gas flow;

when the inhaled gas flow is greater than the fresh gas flow, respectively monitoring a concentration of anesthetic in the inhaled gas and an exhaled gas of the anesthetized object by the anesthetic concentration sensor, thereby correspondingly obtaining an inhaled gas anesthetic concentration and an exhaled gas anesthetic concentration;

using the exhaled gas anesthetic concentration and a concentration of carbon dioxide in the exhaled gas to calculate a concentration of anesthetic in a gas, reflowing into an inspiratory branch, in the exhaled gas, thereby obtaining a re-inhaled gas anesthetic concentration; and using the fresh gas flow, the inhaled gas flow, the inhaled gas anesthetic concentration, and the re-inhaled gas anesthetic concentration to calculate a concentration of output anesthetic of an anesthetic output device, thereby obtaining an anesthetic output concentration.

According to a fourth aspect, the present disclosure discloses an anesthesia machine, including the anesthetic output concentration monitoring device disclosed above.

According to a fifth aspect, the present disclosure further discloses a computer-readable storage medium, configured to store a computer program, wherein the computer program is executed by a processor to implement the steps in the anesthetic output concentration monitoring method.

It may be seen that in the present disclosure, fresh gas flow, inhaled gas flow, an inhaled gas anesthetic concentration, and an exhaled gas anesthetic concentration are first monitored. The concentration of anesthetic in a gas, reflowing into an inspiratory branch, in exhaled gas is then calculated based on the exhaled gas anesthetic concentration and the concentration of carbon dioxide in the exhaled gas, thereby obtaining a re-inhaled gas anesthetic concentration. Next, the concentration of output anesthetic of an anesthetic output device is calculated based on the fresh gas flow, the inhaled gas flow, the inhaled gas anesthetic concentration, and the re-inhaled gas anesthetic concentration, thereby obtaining an anesthetic output concentration. That is, in the present disclosure, the concentration of output anesthetic of an anesthetic output device in an anesthesia machine is calculated based on fresh gas flow, inhaled gas flow, an inhaled gas anesthetic concentration, an exhaled gas anesthetic concentration, and the concentration of carbon dioxide in exhaled gas. The fresh gas flow, the inhaled gas flow, the inhaled gas anesthetic concentration, the exhaled gas anesthetic concentration, and the concentration of carbon dioxide in the exhaled gas may all be monitored based on existing sensors in a current anesthesia machine. Therefore, in the present disclosure, no additional hardware configuration needs to be added in a process of monitoring an anesthetic output concentration of an anesthetic output device, thereby monitoring an anesthetic output concentration at low costs.

BRIEF DESCRIPTION OF THE DRAWINGS

In order to more clearly illustrate technical solutions in the embodiments of the present disclosure or in the prior art, a brief introduction to the drawings is provided below. The drawings in the following description are only some of the embodiments of the present disclosure.

DETAILED DESCRIPTION

The technical solutions of the embodiments of the present application will be described below clearly and comprehensively in conjunction with the drawings of the embodiments of the present disclosure. Clearly, the embodiments described are merely some embodiments of the present disclosure and are not all of the possible embodiments.

Figure 1:
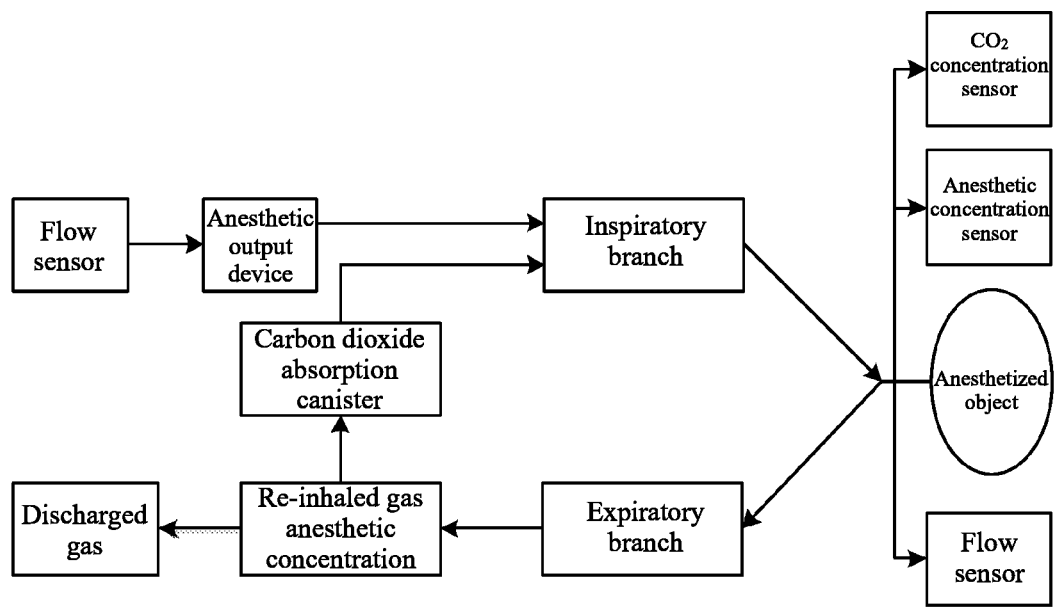
FIG. 1 is a structural diagram of a specific air path in an anesthesia machine.

The technical solution disclosed in the present disclosure is applied to an anesthesia machine. FIG. 1 is a structural diagram of a specific air path of the anesthesia machine. In FIG. 1, when an anesthetized object inhales gas delivered by an inspiratory branch, an exhaled gas branch collects exhaled gas of the anesthetized object. The collected exhaled gas is then delivered to a re-inhaled gas buffer device. The re-inhaled gas buffer device discharges excessive gas in the received gas to the outside and delivers the remaining gas to a carbon dioxide absorption canister to filter out carbon dioxide in the remaining gas. Next, output gas of the carbon dioxide absorption canister and contains no carbon dioxide and output fresh gas carrying anesthetic of an anesthetic output device flow together into the inspiratory branch. In the structural diagram of the air path, the inspiratory branch, the exhaled gas branch, the re-inhaled gas buffer device, and the carbon dioxide absorption canister together form a breathing circuit. In FIG. 1, fresh gas is directly input to the inspiratory branch to implement the input of fresh gas into the breathing circuit. Certainly, fresh gas may be input to another inlet located in the breathing circuit to implement the input of fresh gas into the breathing circuit. For example, fresh gas may be directly input into the carbon dioxide absorption canister for implementation.

It may be understood that, a flow sensor connected to the anesthetic output device in FIG. 1 is specifically configured to monitor a flow of fresh gas flowing into the breathing circuit. The flow sensor located on one side of the anesthetized object is specifically configured to monitor a flow of inhaled gas of the anesthetized object. An anesthetic concentration sensor is specifically configured to monitor an inhaled gas anesthetic concentration and an exhaled gas anesthetic concentration of the anesthetized object. A $CO_2$ concentration sensor is specifically configured to monitor the concentration of carbon dioxide in the exhaled gas of the anesthetized object. It should be noted that the flow sensor connected to the anesthetic output device is specifically a flow sensor located in a flowmeter. The flow sensor located on a side of the anesthetized object is specifically a flow sensor located on a ventilator.

In addition, the anesthetic output device in FIG. 1 may be an evaporator on an existing anesthesia machine or may be a device that directly injects anesthetic to the breathing circuit. Further, the re-inhaled gas buffer device may be a bellow or may be a volume reflector or a gas storage bag having an exhaust function.

Figure 2:
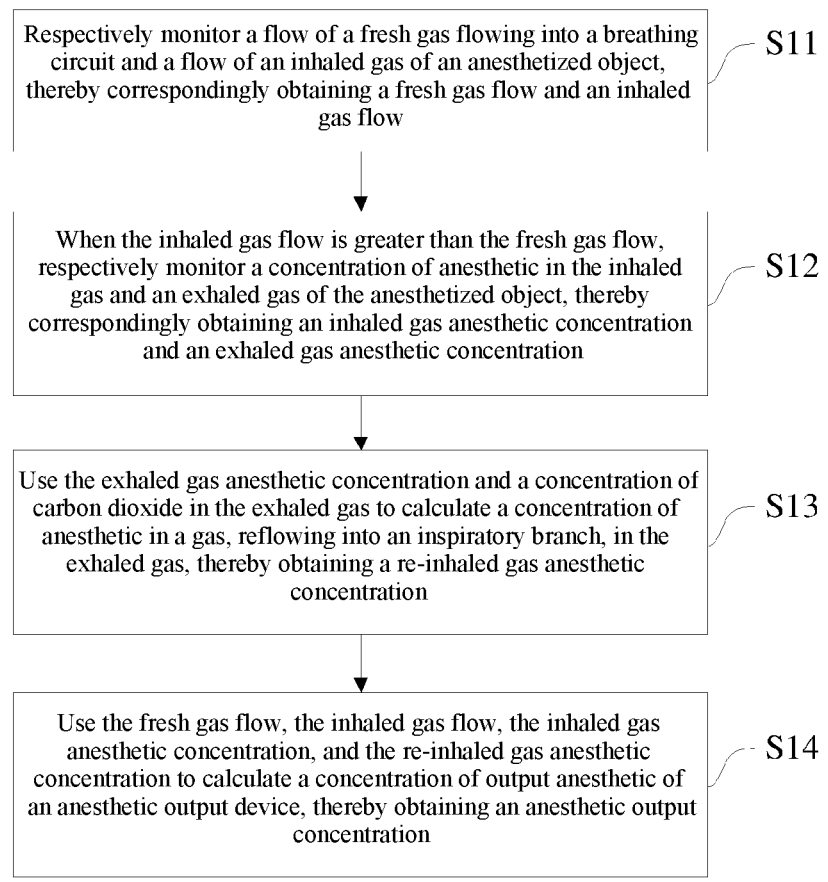
FIG. 2 is a flowchart of an anesthetic output concentration monitoring method according to an embodiment of the present disclosure.

Referring to FIG. 2, an embodiment of the present disclosure discloses an anesthetic output concentration monitoring method. The method includes the following steps.

Step S11: respectively monitoring a flow of a fresh gas flowing into a breathing circuit and a flow of an inhaled gas of an anesthetized object, thereby correspondingly obtaining a fresh gas flow and an inhaled gas flow.

In this embodiment, a flow sensor located on one side of an anesthetic output device may be specifically used to monitor a flow of output fresh gas carrying anesthetic of the anesthetic output device, thereby correspondingly obtaining a fresh gas flow, and measured values of the flow sensors on an inspiratory branch and an exhaled gas branch are used to determine the inhaled gas flow.

In this embodiment, output fresh gas carrying anesthetic of the anesthetic output device may be input into the breathing circuit through an inlet located between a downstream of a carbon dioxide absorption canister and an upstream of the inspiratory branch or may flow into the breathing circuit through another inlet at the breathing circuit. For example, fresh gas may be directly input into the carbon dioxide absorption canister to input fresh gas into the breathing circuit. It further needs to be noted that the carbon dioxide absorption canister in this embodiment may be disposed downstream a re-inhaled gas buffer device. Alternatively, the carbon dioxide absorption canister may be disposed upstream the re-inhaled gas buffer device according to an actual requirement. The present disclosure is described in detail mainly using a specific structure in which the carbon dioxide absorption canister is disposed downstream the re-inhaled gas buffer device.

It may be understood that, the anesthetized object in this embodiment may be a person or may be another animal that requires anesthesia.

Step S12: when the inhaled gas flow is greater than the fresh gas flow, respectively monitoring a concentration of anesthetic in the inhaled gas and an exhaled gas of the anesthetized object, thereby correspondingly obtaining an inhaled gas anesthetic concentration and an exhaled gas anesthetic concentration.

Specifically, when the inhaled gas flow is greater than the fresh gas flow, an anesthetic concentration sensor located on the anesthetized object may be used to monitor the concentration of anesthetic in the inhaled gas of the anesthetized object and the concentration of anesthetic in the exhaled gas. It may be understood that, the sensor configured to monitor the concentration of anesthetic in the inhaled gas of the anesthetized object and the sensor configured to monitor the concentration of anesthetic in the exhaled gas may be the same sensor or may be independent sensors.

If the inhaled gas flow is less than or equal to the fresh gas flow, it means that at this time fresh gas is sufficient for the anesthetized object to breathe. Therefore, in this case, surplus fresh gas and the gas exhaled by the anesthetized object may be discharged outside through an exhaust port of the re-inhaled gas buffer device. In this case, the gas exhaled by the anesthetized object no longer reflows into the inspiratory branch. In this way, the concentration of anesthetic in the inhaled gas of the anesthetized object monitored at this time may be directly determined as the concentration of output anesthetic of the anesthetic output device. That is, after step S11, the method may further include: when the inhaled gas flow is less than or equal to the fresh gas flow, monitoring a concentration of anesthetic in the inhaled gas of the anesthetized object, and directly determining the concentration of anesthetic as the concentration of output anesthetic of the anesthetic output device.

Step S13: calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration.

In this embodiment, a $CO_2$ concentration sensor located on a side of the anesthetized object may be used to monitor the concentration of carbon dioxide in the exhaled gas. the concentration of anesthetic in the gas, reflowing into an inspiratory branch, in the exhaled gas is then calculated based on the exhaled gas anesthetic concentration and the concentration of carbon dioxide in the exhaled gas. It may be seen that, in this embodiment, during the calculation of the concentration of anesthetic in the gas reflowing into the inspiratory branch, no additional hardware device needs to be used. Only the flow sensor and a concentration sensor in an existing anesthesia machine need to be used to obtain various types of necessary information used for calculating the re-inhaled gas anesthetic concentration, that is, obtain the exhaled gas anesthetic concentration and the concentration of carbon dioxide in the exhaled gas.

Step S14: calculating the concentration of output anesthetic of an anesthetic output device based on the fresh gas flow, the inhaled gas flow, the inhaled gas anesthetic concentration, and the re-inhaled gas anesthetic concentration, thereby obtaining an anesthetic output concentration.

In this embodiment, the anesthetic output concentration is specifically calculated based on the fresh gas flow, the inhaled gas flow, the inhaled gas anesthetic concentration, and the re-inhaled gas anesthetic concentration. The fresh gas flow, the inhaled gas flow, and the inhaled gas anesthetic concentration may all be monitored based on the flow sensor and an anesthetic concentration sensor in an existing anesthesia machine. Therefore, no additional hardware device needs to be used in this embodiment. Only the various types of parameter information need to be used to calculate the concentration of output anesthetic of the anesthetic output device, so that an anesthetic output concentration is monitored at low costs.

It may be seen that, in this embodiment of the present disclosure, fresh gas flow, inhaled gas flow, an inhaled gas anesthetic concentration, and an exhaled gas anesthetic concentration are first monitored. The concentration of anesthetic in a gas, reflowing into an inspiratory branch, in exhaled gas is then calculated based on the exhaled gas anesthetic concentration and the concentration of carbon dioxide in the exhaled gas, thereby obtaining a re-inhaled gas anesthetic concentration. Next, the concentration of output anesthetic of an anesthetic output device is calculated based on the fresh gas flow, the inhaled gas flow, the inhaled gas anesthetic concentration, and the re-inhaled gas anesthetic concentration, thereby obtaining an anesthetic output concentration. That is, in this embodiment of the present disclosure, the concentration of output anesthetic of an anesthetic output device in an anesthesia machine is calculated based on fresh gas flow, inhaled gas flow, an inhaled gas anesthetic concentration, an exhaled gas anesthetic concentration, and the concentration of carbon dioxide in exhaled gas. The fresh gas flow, the inhaled gas flow, the inhaled gas anesthetic concentration, the exhaled gas anesthetic concentration, and the concentration of carbon dioxide in the exhaled gas may all be monitored based on existing sensors in a current anesthesia machine. Therefore, in this embodiment of the present disclosure, no additional hardware configuration needs to be added in a process of monitoring an anesthetic output concentration of an anesthetic output device, thereby monitoring an anesthetic output concentration at low costs.

In this embodiment of the present disclosure, a specific process of step S13 in the foregoing embodiment is further described. Specifically, in this embodiment, a plurality of different calculation methods may be used to calculate the concentration of anesthetic in the gas, reflowing into the inspiratory branch, in the exhaled gas. Different calculation methods correspond to different calculation precision. Specifically, in a specific implementation, if a reflowing branch has a smaller length and/or a smaller volume and/or a flow of gas flowing from the reflowing branch to the inspiratory branch is larger, a change degree of a change in the concentration of anesthetic in the reflowing branch due to the factors of the reflowing branch is smaller. In this case, there is a relatively low requirement for calculation precision of the re-inhaled gas anesthetic concentration. Therefore, the process of changes of the concentration caused by a part other than a carbon dioxide absorption canister on the reflowing branch may be ignored. It should be noted that, the exhaled gas branch, the re-inhaled gas buffer device, and the carbon dioxide absorption canister are provided on the reflowing branch. That is, in this embodiment, the step of calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration may specifically include:

calculating the concentration of anesthetic in the gas reflowing into the inspiratory branch in the exhaled gas based on the exhaled gas anesthetic concentration, the concentration of carbon dioxide in the exhaled gas, and a calculation model for the re-inhaled gas anesthetic concentration, thereby obtaining a re-inhaled gas anesthetic concentration;

wherein the calculation model for the re-inhaled gas anesthetic concentration is a model created based on an process of changes in the anesthetic concentration caused by a carbon dioxide absorption canister. Specifically, $$C_{re} = \frac{EtAA}{1 - EtCO_2};$$

wherein in the formula, $C_{re}$ represents the re-inhaled gas anesthetic concentration, EtAA represents the exhaled gas anesthetic concentration, and $EtCO_2$ represents the concentration of carbon dioxide in the exhaled gas.

In another specific implementation, if the length of the reflowing branch has a larger length and/or a larger volume and/or a flow of gas flowing from the reflowing branch to the inspiratory branch is smaller, a change degree of a change in the concentration of anesthetic in the reflowing branch due to the factors of the reflowing branch is larger. In this case, there is a relatively high requirement for calculation precision of the re-inhaled gas anesthetic concentration. Therefore, the process of changes of the concentration caused by a part other than the carbon dioxide absorption canister on the reflowing branch may not be ignored. That is, an analysis result of changes in the anesthetic concentration corresponding to the reflowing branch needs to be combined to calculate the re-inhaled gas anesthetic concentration. That is, in this embodiment, the step of calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration includes:

calculating the concentration of anesthetic in the gas reflowing into the inspiratory branch in the exhaled gas based on the exhaled gas anesthetic concentration, the concentration of carbon dioxide in the exhaled gas, and an analysis result of changes in the anesthetic concentration, thereby obtaining a re-inhaled gas anesthetic concentration;

wherein the analysis result of changes in the anesthetic concentration is a result obtained after an analysis of the process of changes in the anesthetic concentration in a reflowing branch.

In this embodiment, a plurality of different manners may be used, thereby obtaining the analysis result of changes in the anesthetic concentration. Specifically, in a specific implementation, the step of obtaining the analysis result of changes in the anesthetic concentration specifically includes: analyzing the process of changes in the anesthetic concentration in the reflowing branch by means of a delayer and a filter, thereby obtaining the analysis result of changes in the anesthetic concentration. The analysis result of changes in the anesthetic concentration is specifically as follows:

$$C[n] = EtAA[n-k]/(1 - EtCO_2[n-k]);$$
$$C_{re}[n] + b_1 \cdot C_{re}[n-1] + \cdots + b_m \cdot C_{re}[n-m] =$$
$$a_0 C[n] + a_1 \cdot C[n-1] + \cdots + a_l \cdot C[n-l];$$

wherein in the formula, k is a delay coefficient corresponding to the delayer, $\vec{a}=[a_0,a_1,\ldots,a_l]$ and $\vec{b}=[b_0,b_1,\ldots,b_m]$ are coefficients of the filter, and n represents a sampling moment. In this way, it may be known that the filter used herein is specifically a discrete IIR filter. Certainly, in this embodiment, the filter may be replaced with a nonlinear system delivery function in another form.

It should be noted that, the delay coefficient and the coefficient of the filter are both associated with the volume $V_{re}$ of the reflowing branch and a flow MV–FG of gas flowing from the reflowing branch to the inspiratory branch, wherein MV represents the inhaled gas flow, and FG represents the fresh gas flow. During actual application, a corresponding empirical value may be assigned to each foregoing coefficient according to actual experience, or various foregoing coefficients may be determined by means of a function related to $V_{re}$, MV, and FG. For example, $k=f_1(V_{re},MV,FG)$, $\vec{a}=f_2(V_{re},MV,FG)$ and $\vec{b}=f_3(V_{re},MV,FG)$. It may be understood that, when $\vec{b}=0$, the obtained $C_{re}$ is specifically weighted average filtering of a delay of EtAA. In addition, in this embodiment, if the volume $V_{re}$ of the reflowing branch is smaller, the delay coefficient is smaller. If the flow MV–FG of gas flowing from the reflowing branch to the inspiratory branch is larger, the delay coefficient is smaller. It should further be noted that the delay coefficient and the coefficients of the filter are correlated to the volume $V_{re}$ of the reflowing branch and the flow of gas flowing from the reflowing branch to the inspiratory branch, and in addition, because the length of the reflowing branch affects the volume $V_{re}$ of the reflowing branch during actual application, the volume $V_{re}$ of the reflowing branch is also associated with the length of the reflowing branch. Specifically, based on the premise that the reflowing branch has a constant sectional area, in this embodiment, the length of the reflowing branch may be used as an influence factor for determining the delay coefficient and the coefficient of the filter.

In another specific implementation, the step of obtaining the analysis result of changes in the anesthetic concentration may specifically include:

respectively creating corresponding models for the exhaled gas branch, the re-inhaled gas buffer device, and the carbon dioxide absorption canister based on a predetermined gas delivery model that is used to represent a relationship between an inflow gas anesthetic concentration and an outflow gas anesthetic concentration of an analysis object, thereby obtaining an anesthetic concentration analysis result including a first gas delivery model, a second gas delivery model, and a third gas delivery model.

It may be seen that, in this embodiment of the present disclosure, corresponding models for an exhaled gas branch, a re-inhaled gas buffer device, and a carbon dioxide absorption canister are respectively created based on a predetermined gas delivery model that is used to represent a relationship between an inflow gas anesthetic concentration and an outflow gas anesthetic concentration of an analysis object, so as, thereby obtaining an anesthetic concentration analysis result including three gas delivery models. That is, in this embodiment, an exhaled gas branch, a re-inhaled gas buffer device, and a carbon dioxide absorption canister on a reflowing branch may be sequentially used as analysis objects to create three gas delivery models corresponding to the foregoing three analysis objects.

In this embodiment, the predetermined gas delivery model used to represent the relationship between an inflow gas anesthetic concentration and an outflow gas anesthetic concentration of an analysis object may be specifically as follows:

$$(F_{in} \cdot C_{in} - F_{out} \cdot C_{out}) \cdot dt = V_{object} \cdot dC_{out}$$

wherein in the formula, $F_{in}$ represents a flow of gas flowing into the analysis object, $C_{in}$ represents the concentration of anesthetic in gas flowing into the analysis object, $F_{out}$ represents a flow of gas flowing out of the analysis object, $C_{out}$ represents the concentration of anesthetic in gas flowing out of the analysis object, and $V_{object}$ represents the volume of the analysis object. It may be understood that, the physical meaning represented by the predetermined gas delivery model is that an amount of gas that accumulates inside the analysis object is equal to a difference between an amount of gas flowing into the analysis object and an amount of gas flowing out of the analysis object.

In this embodiment, before the exhaled gas of the anesthetized object flows into the re-inhaled gas buffer device from the exhaled gas branch, a flow of gas flowing into the re-inhaled gas buffer device may be equivalent to a flow of the exhaled gas of the anesthetized object, that is, equivalent to a flow of the inhaled gas of the anesthetized object. After gas flows into the re-inhaled gas buffer device, the concentration of anesthetic in gas discharged by the exhaust port is the same as the concentration of anesthetic in gas flowing into the carbon dioxide absorption canister. After gas flows into the carbon dioxide absorption canister, $CO_2$ in the carbon dioxide absorption canister is absorbed, which is equivalent to that a flow of the discharged gas is $F_{CO_2} = F_{absorber} \cdot C_{CO_2}$, wherein $F_{CO_2}$ represents a flow of absorbed $CO_2$ gas in gas flowing into the carbon dioxide absorption canister, $F_{absorber}$ represents a flow of gas flowing from the re-inhaled gas buffer device to the carbon dioxide absorption canister, and $C_{CO_2}$ represents the concentration of $CO_2$ gas in gas flowing into the carbon dioxide absorption canister.

In this embodiment, the first gas delivery model is specifically as follows:

$$(MV \cdot EtAA - F_{bellow} \cdot C_{bellow}) \cdot dt = V_{exp} \cdot dC_{bellow}, \text{ and } F_{bellow} = MV$$

wherein in the formula, MV represents the inhaled gas flow, and the value of the inhaled gas flow is the same as the value of the flow of exhaled gas of the anesthetized object, EtAA represents the exhaled gas anesthetic concentration, $F_{bellow}$ represents a flow of gas flowing from the exhaled gas branch to the re-inhaled gas buffer device, $C_{bellow}$ represents the concentration of anesthetic in gas flowing from the exhaled gas branch to the re-inhaled gas buffer device, and $V_{exp}$ represents the volume of the exhaled gas branch.

In addition, the second gas delivery model is specifically as follows:

$$[MV \cdot C_{bellow} - (F_{absorber} + F_{pop\text{-}off}) \cdot C_{absorber}] \cdot dT = V_{bellow} \cdot dC_{absorber} \text{ and } F_{absorber} + F_{pop\text{-}off} = MV$$

wherein in the formula, $F_{absorber}$ represents a flow of gas flowing from the re-inhaled gas buffer device to the carbon dioxide absorption canister, $F_{pop\text{-}off}$ represents a flow of gas discharged from a pop-off valve of the re-inhaled gas buffer device, $C_{absorber}$ represents the concentration of anesthetic in gas flowing from the re-inhaled gas buffer device to the carbon dioxide absorption canister, and $V_{bellow}$ represents the volume of the re-inhaled gas buffer device.

Further, the third gas delivery model is specifically as follows:

$$[F_{absorber} \cdot C_{absorber} - (F_{absorber} - F_{CO_2}) \cdot C_{re}] \cdot dt = V_{absorber} \cdot dC_{re} \text{ and } F_{absorber} - F_{CO_2} = MV - FG,$$
$$F_{CO_2} = F_{absorber} \cdot C_{CO_2}$$

wherein in the formula, $F_{CO_2}$ represents a flow of absorbed $CO_2$ gas in gas flowing into the carbon dioxide absorption canister, $C_{re}$ represents the re-inhaled gas anesthetic concentration, FG represents the fresh gas flow, $V_{absorber}$ represents the volume of the carbon dioxide absorption canister, $C_{CO_2}$ represents the concentration of $CO_2$ gas in gas flowing into the carbon dioxide absorption canister, $EtCO_2$ represents the concentration of carbon dioxide in the exhaled gas, and $C_{CO_2} = EtCO_2$. That is, in this embodiment, it is assumed by default that the concentration of carbon dioxide in the exhaled gas of the anesthetized object is equal to the concentration of $CO_2$ gas in gas flowing into the carbon dioxide absorption canister.

The three gas delivery models constitute a differential equation group. The exhaled gas anesthetic concentration and the concentration of carbon dioxide in the exhaled gas are combined to gradually solve the differential equation group, so as to calculate the re-inhaled gas anesthetic concentration $C_{re}$. Considering that during actual application, the position order of the exhaled gas branch, the re-inhaled gas buffer device, and the carbon dioxide absorption canister may be flexibly adjusted, and the order of creating three models may be flexibly changed according to actual cases.

In addition, during actual application, when the calculation precision requirement of the re-inhaled gas anesthetic concentration may be appropriately lowered, to reduce the amount of calculation, based on a predetermined gas delivery model that is used to represent a relationship between an inflow gas anesthetic concentration and an outflow gas anesthetic concentration of an analysis object, corresponding models may be created for only the exhaled gas branch and the carbon dioxide absorption canister in the reflowing branch, or corresponding models may only be created for the re-inhaled gas buffer device and the carbon dioxide absorption canister in the reflowing branch, to correspondingly obtain the anesthetic concentration analysis result including two gas delivery models. Subsequently, a corresponding differential solution process may be performed based on the anesthetic concentration analysis result, the exhaled gas anesthetic concentration, and the concentration of carbon dioxide in the exhaled gas to calculate the re-inhaled gas anesthetic concentration $C_{re}$.

Considering that different anesthesia machines have different calculation precision requirements of the re-inhaled gas anesthetic concentration, to satisfy the calculation precision requirement and avoid the generation of a relatively large amount of calculation, in this embodiment, before the step of calculating the concentration of anesthetic in the gas, reflowing into an inspiratory branch, in the exhaled gas based on the exhaled gas anesthetic concentration and the concentration of carbon dioxide in the exhaled gas, the method may further include:

determining the calculation precision requirement of the re-inhaled gas anesthetic concentration, and then determining a corresponding re-inhaled gas anesthetic concentration calculation method according to the calculation precision requirement of the re-inhaled gas anesthetic concentration.

It may be known according to the foregoing embodiment that in the present disclosure, the re-inhaled gas anesthetic concentration may be calculated based on the calculation model for the re-inhaled gas anesthetic concentration or the analysis result of changes in the anesthetic concentration, wherein the calculation precision corresponding to the calculation method based on the former is lower than that corresponding to the calculation method based on the latter. In this embodiment of the present disclosure, appropriate calculation methods may be eventually chosen according to different calculation precision requirements of the re-inhaled gas anesthetic concentration to perform calculation, thereby satisfying the calculation precision requirement and avoiding the generation of a relatively large amount of calculation.

In this embodiment, the step of determining the calculation precision requirement of the re-inhaled gas anesthetic concentration may specifically include:

obtaining a branch parameters of a reflowing branch, wherein the branch parameters of the reflowing branch include a length and/or a volume of the reflowing branch and/or a flow of gas flowing from the reflowing branch to the inspiratory branch; and then determining the calculation precision requirement of the re-inhaled gas anesthetic concentration according to the branch parameters of the reflowing branch.

It may be understood that, if the reflowing branch has a smaller length and/or a smaller volume and/or a flow of gas flowing from the reflowing branch to the inspiratory branch is larger, a change degree of a change in the concentration of anesthetic in the reflowing branch due to the factors of the reflowing branch is smaller. In this case, there is a relatively low requirement for calculation precision of the re-inhaled gas anesthetic concentration.

Figure 3:
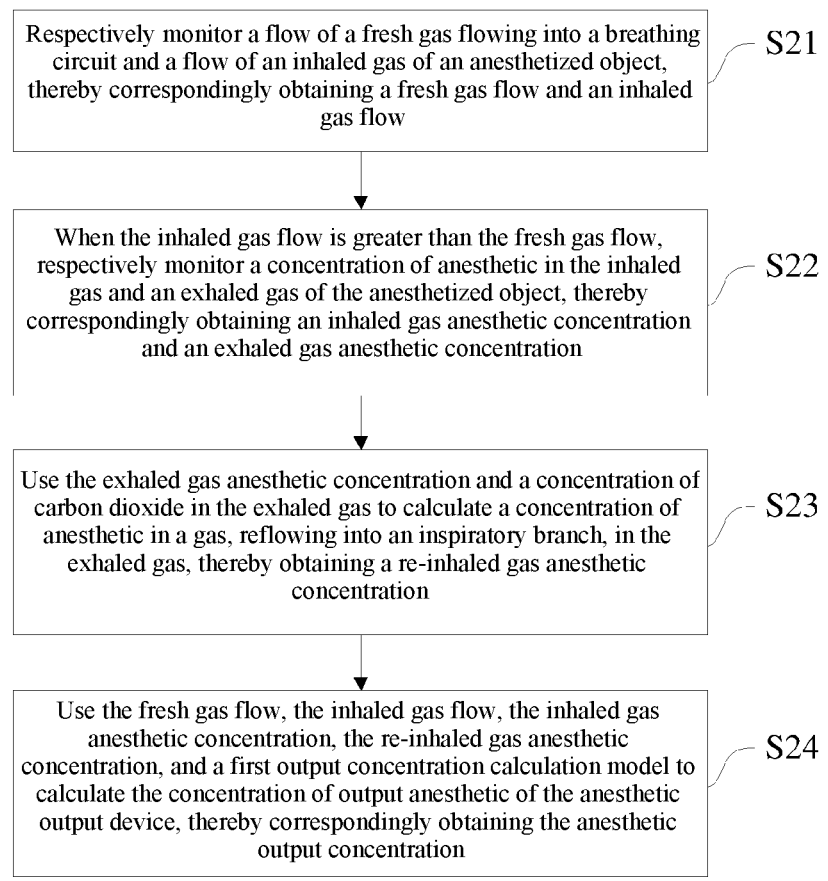
FIG. 3 is a flowchart of a specific anesthetic output concentration monitoring method according to an embodiment of the present disclosure.

Referring to FIG. 3, FIG. 3 shows a specific anesthetic output concentration monitoring method. The method includes the following steps.

Step S21: respectively monitoring a flow of a fresh gas flowing into a breathing circuit and a flow of an inhaled gas of an anesthetized object, thereby correspondingly obtaining a fresh gas flow and an inhaled gas flow.

Step S22: when the inhaled gas flow is greater than the fresh gas flow, respectively monitoring a concentration of anesthetic in the inhaled gas and an exhaled gas of the anesthetized object, thereby correspondingly obtaining an inhaled gas anesthetic concentration and an exhaled gas anesthetic concentration.

Step S23: calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration.

For a specific process of the foregoing steps S21 to S23, reference may be made to related content disclosed in the foregoing embodiments. Details are not described herein again.

Step S24: calculating the concentration of output anesthetic of an anesthetic output device based on the fresh gas flow, the inhaled gas flow, the inhaled gas anesthetic concentration, the re-inhaled gas anesthetic concentration, and a first output concentration calculation model, thereby correspondingly obtaining an anesthetic output concentration.

The first output concentration calculation model is a model created based on the premise that the process of changes in the anesthetic concentration in the inspiratory branch is ignored. In this embodiment, a specific first output concentration calculation model is:

$$C_{vap}=[MV\cdot FiAA-(MV-FG)\cdot C_{re}]/FG$$

wherein in the formula, $C_{vap}$ represents the anesthetic output concentration, MV represents the inhaled gas flow, FiAA represents the inhaled gas anesthetic concentration, FG represents the fresh gas flow, and $C_{re}$ represents the re-inhaled gas anesthetic concentration.

It may be understood that, the first output concentration calculation model is a calculation model determined based on the premise that the changes in concentration in the inspiratory branch is ignored, and has advantages of simple and fast calculation. In addition, all data required in the foregoing calculation process are monitored by existing sensors in an existing anesthesia machine without relying on additional hardware, so that an anesthetic output concentration is monitored at low costs.

To improve the reliability of the anesthetic output device and avoid medical malpractice caused by a machine fault, this embodiment of the present disclosure may further include: determining whether the anesthetic output concentration is greater than a preset output concentration threshold, and if yes, triggering a corresponding abnormal response operation.

It should be noted that, the preset output concentration threshold is specifically a preset parameter value limited by a hardware condition of the anesthetic output device and/or a physical condition of the anesthetized object, and may be set by a user by means of a preset parameter setting interface, or may be automatically set by a system according to information such as the model and/or use duration of the anesthetic output device and/or a physical condition of an anesthetized object. In addition, the abnormal response operation includes, but is not limited to, sending alarm information and/or turning off the anesthetic output device.

Further, to make it convenient for a user to intuitively learn about the consumption of anesthetic in the anesthetic output device, this embodiment of the present disclosure may further include: calculating and displaying an anesthetic consumption rate and/or an anesthetic consumption amount in the anesthetic output device based on the anesthetic output concentration and the fresh gas flow.

Specifically, the anesthetic consumption rate may be obtained by multiplying the anesthetic output concentration by the fresh gas flow. In addition, in this embodiment, according to a preset consumption amount statistics period, the anesthetic consumption amount of the anesthetic output device in a last consumption amount statistic period may be periodically calculated based on the anesthetic output concentration and the fresh gas flow. Next, the calculated anesthetic consumption rate and/or anesthetic consumption amount is delivered to a display screen of an anesthesia machine or a display screen of another external device for display.

Figure 4:
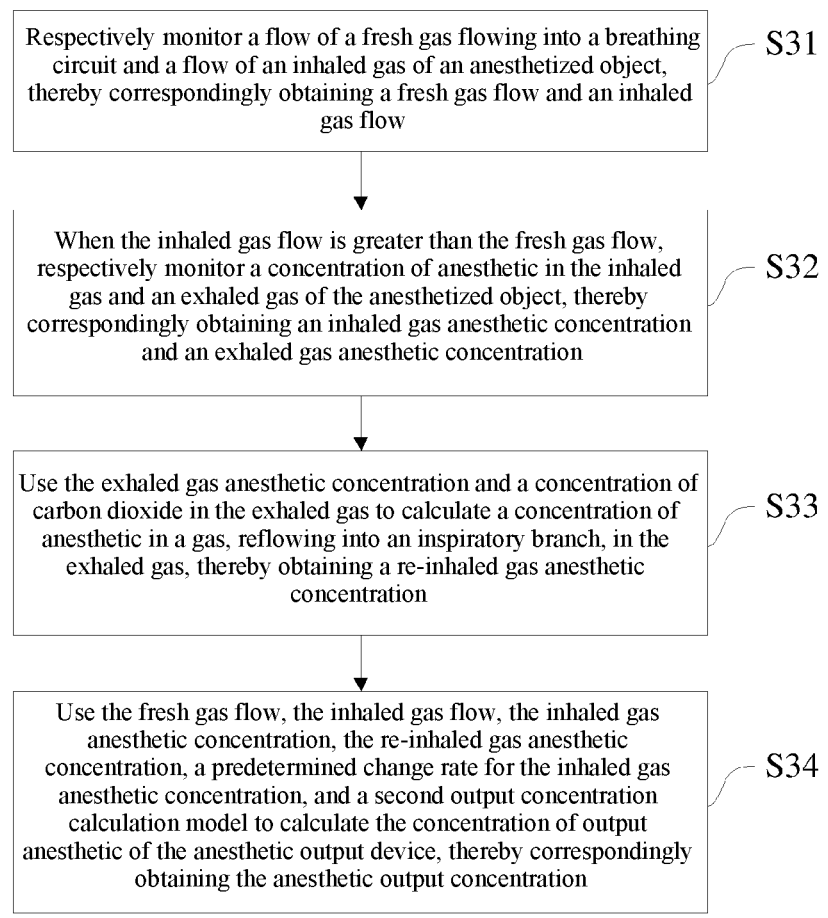
FIG. 4 is a flowchart of another specific anesthetic output concentration monitoring method according to an embodiment of the present disclosure.

Referring to FIG. 4, FIG. 4 shows a specific anesthetic output concentration monitoring method. The method includes the following steps.

Step S31: respectively monitoring a flow of a fresh gas flowing into a breathing circuit and a flow of an inhaled gas of an anesthetized object, thereby correspondingly obtaining a fresh gas flow and an inhaled gas flow.

Step S32: when the inhaled gas flow is greater than the fresh gas flow, respectively monitoring a concentration of anesthetic in the inhaled gas and an exhaled gas of the anesthetized object, thereby correspondingly obtaining an inhaled gas anesthetic concentration and an exhaled gas anesthetic concentration.

Step S33: calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration.

For a specific process of the foregoing steps S31 to S33, reference may be made to related content disclosed in the foregoing embodiments. Details are not described herein again.

Step S34: calculating the concentration of output anesthetic of an anesthetic output device based on the fresh gas flow, the inhaled gas flow, the inhaled gas anesthetic concentration, the re-inhaled gas anesthetic concentration, a predetermined change rate for the inhaled gas anesthetic concentration, and a second output concentration calculation model, thereby correspondingly obtaining an anesthetic output concentration.

The second output concentration calculation model is a model created considering an process of changes in the anesthetic concentration in the inspiratory branch. In this embodiment, a specific second output concentration calculation model is:

$$FG \cdot C_{vap} + (MV - FG) \cdot C_{re} - MV \cdot FiAA = V_{insp} \cdot \Delta FiAA$$

wherein in the formula, FG represents the fresh gas flow, $C_{vap}$ represents the anesthetic output concentration, MV represents the inhaled gas flow, $C_{re}$ represents the re-inhaled gas anesthetic concentration, FiAA represents the inhaled gas anesthetic concentration, $V_{insp}$ represents the volume of the inspiratory branch, $\Delta FiAA$ represents a change rate of the inhaled gas anesthetic concentration, and the change rate may be obtained by calculating the derivative or differential of the inhaled gas anesthetic concentration.

It may be understood that, the second output concentration calculation model is a calculation model determined considering a change in the concentration of the inspiratory branch and has advantage of precise calculation. In addition, all data required in the foregoing calculation process are monitored by existing sensors in an existing anesthesia machine without relying on additional hardware, so that the anesthetic output concentration is monitored at low costs.

To improve the reliability of the anesthetic output device and avoid medical malpractice caused by a machine fault, this embodiment of the present disclosure may further include: determining whether the anesthetic output concentration is greater than a preset output concentration threshold, and if yes, triggering a corresponding abnormal response operation.

It should be noted that, the preset output concentration threshold is specifically a preset parameter value limited by a hardware condition of the anesthetic output device and/or a physical condition of the anesthetized object, and may be set by a user by means of a preset parameter setting interface, or may be automatically set by a system according to information such as the model and/or use duration of the anesthetic output device and/or a physical condition of an anesthetized object. In addition, the abnormal response operation includes, but is not limited to, sending alarm information and/or turning off the anesthetic output device.

Further, to make it convenient for a user to intuitively learn about the consumption of anesthetic in the anesthetic output device, this embodiment of the present disclosure may further include: calculating and displaying an anesthetic consumption rate and/or an anesthetic consumption amount in the anesthetic output device based on the anesthetic output concentration and the fresh gas flow.

Specifically, the anesthetic consumption rate may be obtained by multiplying the anesthetic output concentration by the fresh gas flow. In addition, in this embodiment, according to a preset consumption amount statistics period, the anesthetic consumption amount of the anesthetic output device in a last consumption amount statistic period may be periodically calculated based on the anesthetic output concentration and the fresh gas flow. Next, the calculated anesthetic consumption rate and/or anesthetic consumption amount is delivered to a display screen of an anesthesia machine or a display screen of another external device for display.

Figure 5:
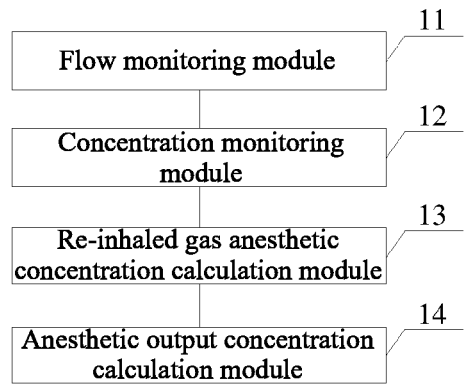
FIG. 5 is a schematic structural diagram of an anesthetic output concentration monitoring system according to an embodiment of the present disclosure.

An embodiment of the present disclosure further correspondingly discloses an anesthetic output concentration monitoring system. Referring to FIG. 5, the system includes:

a flow monitoring module 11, configured to respectively monitor a flow of a fresh gas flowing into a breathing circuit and a flow of an inhaled gas of an anesthetized object, thereby correspondingly obtaining a fresh gas flow and an inhaled gas flow;

a concentration monitoring module 12 configured to when the inhaled gas flow is greater than the fresh gas flow, respectively monitor a concentration of anesthetic in the inhaled gas and an exhaled gas of the anesthetized object, thereby correspondingly obtaining an inhaled gas anesthetic concentration and an exhaled gas anesthetic concentration;

a re-inhaled gas anesthetic concentration calculation module 13, configured to calculate the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration; and an anesthetic output concentration calculation module 14, configured to calculate the concentration of output anesthetic of an anesthetic output device based on the fresh gas flow, the inhaled gas flow, the inhaled gas anesthetic concentration, and the re-inhaled gas anesthetic concentration, thereby obtaining an anesthetic output concentration.

It may be seen that, in this embodiment of the present disclosure, the concentration of output anesthetic of an anesthetic output device in an anesthesia machine is calculated based on fresh gas flow, inhaled gas flow, an inhaled gas anesthetic concentration, an exhaled gas anesthetic concentration, and the concentration of carbon dioxide in exhaled gas. The fresh gas flow, the inhaled gas flow, the inhaled gas anesthetic concentration, the exhaled gas anesthetic concentration, and the concentration of carbon dioxide in the exhaled gas may all be monitored based on existing sensors in a current anesthesia machine. Therefore, in this embodiment of the present disclosure, no additional hardware configuration needs to be added in a process of monitoring an anesthetic output concentration of an anesthetic output device, thereby monitoring an anesthetic output concentration at low costs.

In a specific implementation, the re-inhaled gas anesthetic concentration calculation module 13 is specifically configured to calculate the concentration of anesthetic in the gas reflowing into the inspiratory branch in the exhaled gas based on the exhaled gas anesthetic concentration, the concentration of carbon dioxide in the exhaled gas, and a calculation model for the re-inhaled gas anesthetic concentration, thereby obtaining a re-inhaled gas anesthetic concentration, wherein wherein the calculation model for the re-inhaled gas anesthetic concentration is a model created based on an process of changes in the anesthetic concentration caused by a carbon dioxide absorption canister. Specifically, $$C_{re} = \frac{EtAA}{1-EtCO_2}$$

wherein in the formula, $C_{re}$ represents the re-inhaled gas anesthetic concentration, EtAA represents the exhaled gas anesthetic concentration, and $EtCO_2$ represents the concentration of carbon dioxide in the exhaled gas.

In another specific implementation, the re-inhaled gas anesthetic concentration calculation module 13 is specifically configured to calculate the concentration of anesthetic in the gas reflowing into the inspiratory branch in the exhaled gas based on the exhaled gas anesthetic concentration, the concentration of carbon dioxide in the exhaled gas, and an analysis result of changes in the anesthetic concentration, thereby obtaining a re-inhaled gas anesthetic concentration;

wherein the analysis result of changes in the anesthetic concentration is a result obtained after an analysis of the process of changes in the anesthetic concentration in a reflowing branch, with an exhaled gas branch, a re-inhaled gas buffer device, and a carbon dioxide absorption canister being provided on the reflowing branch.

In a specific implementation, the re-inhaled gas anesthetic concentration calculation module 13 may further include: a first analysis module, configured to analyze the process of changes in the anesthetic concentration in the reflowing branch by means of a delayer and a filter, thereby obtaining the analysis result of changes in the anesthetic concentration. Correspondingly, the analysis result of changes in the anesthetic concentration is specifically as follows:

$$C[n] = EtAA[n-k]/(1-EtCO_2[n-k])$$
$$C_{re}[n] + b_1 \cdot C_{re}[n-1] + \cdots + b_m \cdot C_{re}[n-m] =$$
$$a_0 C[n] + a_1 \cdot C[n-1] + \cdots + a_l \cdot C[n-l]$$

wherein in the formula, k is a delay coefficient corresponding to the delayer, and $\vec{a}=[a_0, a_1, \ldots, a_l]$ and $\vec{b}=[b_0, b_1, \ldots, b_m]$ are coefficients of the filter. In this way, it may be known that the filter used herein is specifically a discrete IIR filter. Certainly, in this embodiment, the filter may be replaced with a nonlinear system delivery function in another form.

In another specific implementation, the re-inhaled gas anesthetic concentration calculation module may further include: a second analysis module, configured to respectively create corresponding models for the exhaled gas branch, the re-inhaled gas buffer device, and the carbon dioxide absorption canister based on a predetermined gas delivery model that is used to represent a relationship between an inflow gas anesthetic concentration and an outflow gas anesthetic concentration of an analysis object, thereby obtaining an anesthetic concentration analysis result including a first gas delivery model, a second gas delivery model, and a third gas delivery model. Correspondingly, the first gas delivery model, the second gas delivery model, and the third gas delivery model are specifically as follows:

the first gas delivery model is:

$$(MV \cdot EtAA - F_{bellow} \cdot C_{bellow}) \cdot dt = V_{exp} \cdot dC_{bellow}, \text{ and}$$
$$F_{bellow} = MV;$$

wherein in the formula, MV represents the inhaled gas flow, the value of the inhaled gas flow is the same as the value of a flow of the exhaled gas of the anesthetized object, EtAA represents the exhaled gas anesthetic concentration, $F_{bellow}$ represents a flow of gas flowing from the exhaled gas branch to the re-inhaled gas buffer device, $C_{bellow}$ represents the concentration of anesthetic in gas flowing from the exhaled gas branch to the re-inhaled gas buffer device, and $V_{exp}$ represents the volume of the exhaled gas branch;

the second gas delivery model is:

$$[MV \cdot C_{bellow} - (F_{absorber} + F_{pop-off}) \cdot C_{absorber}] \cdot$$
$$dt = V_{bellow} \cdot dC_{absorber}, \text{ and } F_{absorber} + F_{pop-off} = MV$$

wherein in the formula, $F_{absorber}$ represents a flow of gas flowing from the re-inhaled gas buffer device to the carbon dioxide absorption canister, $F_{pop-off}$ represents a flow of gas discharged from a pop-off valve of the re-inhaled gas buffer device, $C_{absorber}$ represents the concentration of anesthetic in gas flowing from the re-inhaled gas buffer device to the carbon dioxide absorption canister, and $V_{bellow}$ represents the volume of the re-inhaled gas buffer device; and the third gas delivery model is:

$$[F_{absorber} \cdot C_{absorber} - (F_{absorber} - F_{CO_2}) \cdot C_{re}] \cdot$$
$$dt = V_{absorber} \cdot dC_{re} \text{ and } F_{absorber} - F_{CO_2} = MV - FG,$$
$$F_{CO_2} = F_{absorber} \cdot C_{CO_2}$$

wherein in the formula, $F_{CO_2}$ represents a flow of absorbed $CO_2$ gas in gas flowing into the carbon dioxide absorption canister, $C_{re}$ represents the re-inhaled gas anesthetic concentration, FG represents the fresh gas flow, $V_{absorber}$ represents the volume of the carbon dioxide absorption canister, $C_{CO_2}$ represents the concentration of $CO_2$ gas in gas flowing into the carbon dioxide absorption canister, $EtCO_2$ represents the concentration of carbon dioxide in the exhaled gas, and $C_{CO_2} = EtCO_1$.

Based on the foregoing embodiment, the anesthetic output concentration monitoring system in the present disclosure may further include:

a precision requirement determination module configured to, before the re-inhaled gas anesthetic concentration calculation module calculates the re-inhaled gas anesthetic concentration, determine the calculation precision requirement of the re-inhaled gas anesthetic concentration; and a calculation method determination module configured to determine a corresponding re-inhaled gas anesthetic concentration calculation method according to the calculation precision requirement of the re-inhaled gas anesthetic concentration.

The precision requirement determination module may specifically include:

a branch parameters acquisition unit configured to, before the re-inhaled gas anesthetic concentration calculation module calculates the re-inhaled gas anesthetic concentration, obtain a branch parameters of a reflowing branch, wherein the branch parameters of the reflowing branch include a length and/or a volume of the reflowing branch and/or a flow of gas flowing from the reflowing branch to the inspiratory branch; and a precision requirement determination unit configured to determine the calculation precision requirement of the re-inhaled gas anesthetic concentration according to the branch parameters of the reflowing branch.

Based on the foregoing embodiment, the monitoring system in the present disclosure may further include:

an anesthetic output concentration direct determination module configured to, after the flow monitoring module monitors the fresh gas flow and the inhaled gas flow, when the inhaled gas flow is less than or equal to the fresh gas flow, monitor a concentration of anesthetic in the inhaled gas of the anesthetized object based on the concentration monitoring module, and directly determine the concentration of anesthetic as the concentration of output anesthetic of the anesthetic output device.

In a specific implementation, the anesthetic output concentration calculation module 14 is specifically configured to calculate the concentration of output anesthetic of the anesthetic output device based on the fresh gas flow, the inhaled gas flow, the inhaled gas anesthetic concentration, the re-inhaled gas anesthetic concentration, and a first output concentration calculation model, thereby correspondingly obtaining an anesthetic output concentration.

The first output concentration calculation model is a model created based on the premise that the process of changes in the anesthetic concentration in the inspiratory branch is ignored. In this embodiment, a specific first output concentration calculation model is:

$$C_{vap}=[MV \cdot FiAA-(MV-FG) \cdot C_{re}]/FG$$

wherein in the formula, $C_{vap}$ represents the anesthetic output concentration, MV represents the inhaled gas flow, FiAA represents the inhaled gas anesthetic concentration, FG represents the fresh gas flow, and $C_{re}$ represents the re-inhaled gas anesthetic concentration.

In another specific implementation, the anesthetic output concentration calculation module 14 is specifically configured to calculate the concentration of output anesthetic of the anesthetic output device based on the fresh gas flow, the inhaled gas flow, the inhaled gas anesthetic concentration, the re-inhaled gas anesthetic concentration, a predetermined change rate for the inhaled gas anesthetic concentration, and a second output concentration calculation model, thereby correspondingly obtaining an anesthetic output concentration.

The second output concentration calculation model is a model created considering an process of changes in the anesthetic concentration in the inspiratory branch. In this embodiment, a specific second output concentration calculation model is:

$$FG \cdot C_{vap}+(MV-FG) \cdot C_{re}-MV \cdot FiAA=V_{insp} \cdot \Delta FiAA$$

wherein in the formula, FG represents the fresh gas flow, $C_{vap}$ represents the anesthetic output concentration, MV represents the inhaled gas flow, $C_{re}$ represents the re-inhaled gas anesthetic concentration, FiAA represents the inhaled gas anesthetic concentration, $V_{insp}$ represents the volume of the inspiratory branch, and $\Delta FiAA$ represents a change rate of the inhaled gas anesthetic concentration.

To improve the reliability of the anesthetic output device and avoid medical malpractice caused by a machine fault, this embodiment of the present disclosure may further include:

a concentration determination module configured to determine whether the anesthetic output concentration is greater than a preset output concentration threshold, and if yes, trigger a corresponding abnormal response operation.

It should be noted that, the preset output concentration threshold may be set by a user by means of a preset parameter setting interface, or may be automatically set by a system according to information such as the model and/or use duration of the anesthetic output device and/or a physical condition of an anesthetized object. In addition, the abnormal response operation includes, but is not limited to, sending alarm information and/or turning off the anesthetic output device.

Further, to make it convenient for a user to intuitively learn about an anesthetic consumption rate and/or an anesthetic consumption amount in the anesthetic output device, this embodiment of the present disclosure may further include:

an anesthetic consumption monitoring module, configured to calculate an anesthetic consumption rate and/or an anesthetic consumption amount in the anesthetic output device based on the anesthetic output concentration and the fresh gas flow, and send the anesthetic consumption rate and/or the anesthetic consumption amount to a preset display screen for display.

Figure 6:
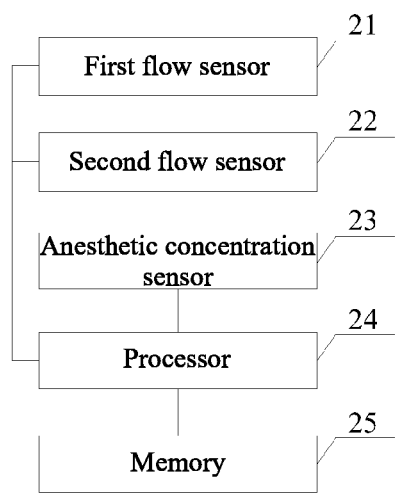
FIG. 6 is a schematic structural diagram of an anesthetic output concentration monitoring device according to an embodiment of the present disclosure.

Referring to FIG. 6, an embodiment of the present disclosure further discloses an anesthetic output concentration monitoring device, including a first flow sensor 21, a second flow sensor 22, an anesthetic concentration sensor 23, a processor 24, and a memory 25. The processor 24 is configured to execute a computer program stored in the memory 25 to implement the following steps:

monitoring, by the first flow sensor 21, a flow of fresh gas flowing into a breathing circuit, thereby correspondingly obtaining a fresh gas flow; monitoring, by the second flow sensor 22, a flow of inhaled gas of an anesthetized object, thereby correspondingly obtaining an inhaled gas flow; when the inhaled gas flow is greater than the fresh gas flow, respectively monitoring, by the anesthetic concentration sensor 23, a concentration of anesthetic in the inhaled gas and an exhaled gas of the anesthetized object, thereby correspondingly obtaining an inhaled gas anesthetic concentration and an exhaled gas anesthetic concentration; calculating the concentration of anesthetic in the gas, reflowing into an inspiratory branch, in the exhaled gas based on the exhaled gas anesthetic concentration and the concentration of carbon dioxide in the exhaled gas, thereby obtaining a re-inhaled gas anesthetic concentration; and calculating the concentration of output anesthetic of an anesthetic output device based on the fresh gas flow, the inhaled gas flow, the inhaled gas anesthetic concentration, and the re-inhaled gas anesthetic concentration, thereby obtaining an anesthetic output concentration.

It should be noted that the second flow sensor 22 may be specifically a flow sensor on a ventilator.

In some embodiments of the present disclosure, the processor 24 may further be configured to execute the computer program in the memory 25 to implement the following step:

calculating the concentration of anesthetic in the gas reflowing into the inspiratory branch in the exhaled gas based on the exhaled gas anesthetic concentration, the concentration of carbon dioxide in the exhaled gas, and a calculation model for the re-inhaled gas anesthetic concentration, thereby obtaining a re-inhaled gas anesthetic concentration, wherein the calculation model for the re-inhaled gas anesthetic concentration is a model created based on an process of changes in the anesthetic concentration caused by a carbon dioxide absorption canister. Specifically, $$C_{re} = \frac{EtAA}{1 - EtCO_2}$$

wherein in the formula, $C_{re}$ represents the re-inhaled gas anesthetic concentration, EtAA represents the exhaled gas anesthetic concentration, and $EtCO_2$ represents the concentration of carbon dioxide in the exhaled gas.

In some embodiments of the present disclosure, the processor 24 may further be configured to execute the computer program in the memory 25 to implement the following step:

calculating the concentration of anesthetic in the gas reflowing into the inspiratory branch in the exhaled gas based on the exhaled gas anesthetic concentration, the concentration of carbon dioxide in the exhaled gas, and an analysis result of changes in the anesthetic concentration, thereby obtaining a re-inhaled gas anesthetic concentration, wherein the analysis result of changes in the anesthetic concentration is a result obtained after an analysis of the process of changes in the anesthetic concentration in a reflowing branch, with an exhaled gas branch, a re-inhaled gas buffer device, and a carbon dioxide absorption canister being provided on the reflowing branch.

In some embodiments of the present disclosure, the processor 24 may further be configured to execute the computer program in the memory 25 to implement the following step:

analyzing the process of changes in the anesthetic concentration in the reflowing branch by means of a delayer and a filter, thereby obtaining the analysis result of changes in the anesthetic concentration.

In some embodiments of the present disclosure, the processor 24 may further be configured to execute the computer program in the memory 25 to implement the following step:

respectively creating corresponding models for the exhaled gas branch, the re-inhaled gas buffer device, and the carbon dioxide absorption canister based on a predetermined gas delivery model that is used to represent a relationship between an inflow gas anesthetic concentration and an outflow gas anesthetic concentration of an analysis object, thereby obtaining an anesthetic concentration analysis result including a first gas delivery model, a second gas delivery model, and a third gas delivery model.

In some embodiments of the present disclosure, the processor 24 may further be configured to execute the computer program in the memory 25 to implement the following step:

before the step of calculating the concentration of anesthetic in the gas, reflowing into an inspiratory branch, in the exhaled gas, determining the calculation precision requirement of the re-inhaled gas anesthetic concentration; and determining a corresponding re-inhaled gas anesthetic concentration calculation method according to the calculation precision requirement of the re-inhaled gas anesthetic concentration.

In some embodiments of the present disclosure, the processor 24 may further be configured to execute the computer program in the memory 25 to implement the following step:

obtaining a branch parameters of a reflowing branch, wherein the branch parameters of the reflowing branch include a length and/or a volume of the reflowing branch and/or a flow of gas flowing from the reflowing branch to the inspiratory branch; and determining the calculation precision requirement of the re-inhaled gas anesthetic concentration according to the branch parameters of the reflowing branch.

In some embodiments of the present disclosure, the processor 24 may further be configured to execute the computer program in the memory 25 to implement the following step:

when the inhaled gas flow is less than or equal to the fresh gas flow, monitoring a concentration of anesthetic in the inhaled gas of the anesthetized object, and directly determining the concentration of anesthetic as the concentration of output anesthetic of the anesthetic output device.

In some embodiments of the present disclosure, the processor 24 may further be configured to execute the computer program in the memory 25 to implement the following step:

calculating the concentration of output anesthetic of the anesthetic output device based on the fresh gas flow, the inhaled gas flow, the inhaled gas anesthetic concentration, the re-inhaled gas anesthetic concentration, and a first output concentration calculation model, thereby correspondingly obtaining an anesthetic output concentration.

The first output concentration calculation model is a model created based on the premise that the process of changes in the anesthetic concentration in the inspiratory branch is ignored. In this embodiment, a specific first output concentration calculation model is:

$$C_{vap} = [MV \cdot FiAA - (MV - FG) \cdot C_{re}]/FG$$

wherein in the formula, $C_{vap}$ represents the anesthetic output concentration, MV represents the inhaled gas flow, FiAA represents the inhaled gas anesthetic concentration, FG represents the fresh gas flow, and Ge represents the re-inhaled gas anesthetic concentration.

In some embodiments of the present disclosure, the processor 24 may further be configured to execute the computer program in the memory 25 to implement the following step:

calculating the concentration of output anesthetic of the anesthetic output device based on the fresh gas flow, the inhaled gas flow, the inhaled gas anesthetic concentration, the re-inhaled gas anesthetic concentration, a predetermined change rate for the inhaled gas anesthetic concentration, and a second output concentration calculation model, thereby correspondingly obtaining an anesthetic output concentration.

The second output concentration calculation model is a model created considering an process of changes in the anesthetic concentration in the inspiratory branch. In this embodiment, a specific second output concentration calculation model is:

$$FG \cdot C_{vap} + (MV - FG) \cdot C_{re} - MV \cdot FiAA = V_{insp} \cdot \Delta FiAA$$

wherein in the formula, FG represents the fresh gas flow, $C_{vap}$ represents the anesthetic output concentration, MV represents the inhaled gas flow, $C_{re}$ represents the re-inhaled gas anesthetic concentration, FiAA represents the inhaled gas anesthetic concentration, $V_{insp}$ represents the volume of the inspiratory branch, and $\Delta FiAA$ represents a change rate of the inhaled gas anesthetic concentration.

In some embodiments of the present disclosure, the processor 24 may further be configured to execute the computer program in the memory 25 to implement the following step:

determining whether the anesthetic output concentration is greater than a preset output concentration threshold, and if yes, triggering a corresponding abnormal response operation.

In some embodiments of the present disclosure, the processor 24 may further be configured to execute the computer program in the memory 25 to implement the following step:

calculating and displaying an anesthetic consumption rate and/or an anesthetic consumption amount in the anesthetic output device based on the anesthetic output concentration and the fresh gas flow.

It may be seen that, in this embodiment of the present disclosure, the concentration of output anesthetic of an anesthetic output device in an anesthesia machine is calculated based on fresh gas flow, inhaled gas flow, an inhaled gas anesthetic concentration, an exhaled gas anesthetic concentration, and the concentration of carbon dioxide in exhaled gas. The fresh gas flow, the inhaled gas flow, the inhaled gas anesthetic concentration, the exhaled gas anesthetic concentration, and the concentration of carbon dioxide in the exhaled gas may all be monitored based on existing sensors in a current anesthesia machine. Therefore, in this embodiment of the present disclosure, no additional hardware configuration needs to be added in a process of monitoring an anesthetic output concentration of an anesthetic output device, thereby monitoring an anesthetic output concentration at low costs.

Further, an embodiment of the present disclosure further discloses an anesthesia machine, including the anesthetic output concentration monitoring device disclosed in the foregoing embodiments. For the specific structure of the anesthetic output concentration monitoring device, reference may be made to the foregoing embodiments. Details are not described herein again.

In addition, an embodiment of the present disclosure further discloses a computer-readable storage medium, configured to store a computer program, wherein the computer program is executed by a processor to implement the steps in the anesthetic output concentration monitoring method disclosed in the foregoing embodiments.

In some embodiments of the present disclosure, when the computer program stored in the computer-readable storage medium is executed by the processor, the processor may further be specifically configured to perform the following step:

calculating the concentration of anesthetic in the gas reflowing into the inspiratory branch in the exhaled gas based on the exhaled gas anesthetic concentration, the concentration of carbon dioxide in the exhaled gas, and a calculation model for the re-inhaled gas anesthetic concentration, thereby obtaining a re-inhaled gas anesthetic concentration, wherein the calculation model for the re-inhaled gas anesthetic concentration is a model created based on an process of changes in the anesthetic concentration caused by a carbon dioxide absorption canister. Specifically, $$C_{re} = \frac{EtAA}{1 - EtCO_2};$$

wherein in the formula, $C_{re}$ represents the re-inhaled gas anesthetic concentration, $EtAA$ represents the exhaled gas anesthetic concentration, and $EtCO_2$ represents the concentration of carbon dioxide in the exhaled gas.

In some embodiments of the present disclosure, when the computer program stored in the computer-readable storage medium is executed by the processor, the processor may further be specifically configured to perform the following step:

calculating the concentration of anesthetic in the gas reflowing into the inspiratory branch in the exhaled gas based on the exhaled gas anesthetic concentration, the concentration of carbon dioxide in the exhaled gas, and an analysis result of changes in the anesthetic concentration, thereby obtaining a re-inhaled gas anesthetic concentration, wherein the analysis result of changes in the anesthetic concentration is a result obtained after an analysis of the process of changes in the anesthetic concentration in a reflowing branch, with an exhaled gas branch, a re-inhaled gas buffer device, and a carbon dioxide absorption canister being provided on the reflowing branch.

In some embodiments of the present disclosure, when the computer program stored in the computer-readable storage medium is executed by the processor, the processor may further be specifically configured to perform the following step:

analyzing the process of changes in the anesthetic concentration in the reflowing branch by means of a delayer and a filter, thereby obtaining the analysis result of changes in the anesthetic concentration.

In some embodiments of the present disclosure, when the computer program stored in the computer-readable storage medium is executed by the processor, the processor may further be specifically configured to perform the following step:

respectively creating corresponding models for the exhaled gas branch, the re-inhaled gas buffer device, and the carbon dioxide absorption canister based on a predetermined gas delivery model that is used to represent a relationship between an inflow gas anesthetic concentration and an outflow gas anesthetic concentration of an analysis object, thereby obtaining an anesthetic concentration analysis result including a first gas delivery model, a second gas delivery model, and a third gas delivery model.

In some embodiments of the present disclosure, when the computer program stored in the computer-readable storage medium is executed by the processor, the processor may further be specifically configured to perform the following step:

before the step of calculating the concentration of anesthetic in the gas, reflowing into an inspiratory branch, in the exhaled gas, determining the calculation precision requirement of the re-inhaled gas anesthetic concentration; and determining a corresponding re-inhaled gas anesthetic concentration calculation method according to the calculation precision requirement of the re-inhaled gas anesthetic concentration.

In some embodiments of the present disclosure, when the computer program stored in the computer-readable storage medium is executed by the processor, the processor may further be specifically configured to perform the following step:

obtaining a branch parameters of a reflowing branch, wherein the branch parameters of the reflowing branch include a length and/or a volume of the reflowing branch and/or a flow of gas flowing from the reflowing branch to the inspiratory branch; and determining the calculation precision requirement of the re-inhaled gas anesthetic concentration according to the branch parameters of the reflowing branch.

In some embodiments of the present disclosure, when the computer program stored in the computer-readable storage medium is executed by the processor, the processor may further be specifically configured to perform the following step:

when the inhaled gas flow is less than or equal to the fresh gas flow, monitoring a concentration of anesthetic in the inhaled gas of the anesthetized object, and directly determining the concentration of anesthetic as the concentration of output anesthetic of the anesthetic output device.

In some embodiments of the present disclosure, when the computer program stored in the computer-readable storage medium is executed by the processor, the processor may further be specifically configured to perform the following step:

calculating the concentration of output anesthetic of the anesthetic output device based on the fresh gas flow, the inhaled gas flow, the inhaled gas anesthetic concentration, the re-inhaled gas anesthetic concentration, and a first output concentration calculation model, thereby correspondingly obtaining an anesthetic output concentration.

The first output concentration calculation model is a model created based on the premise that the process of changes in the anesthetic concentration in the inspiratory branch is ignored. In this embodiment, a specific first output concentration calculation model is:

$$C_{vap}=[MV \cdot FiAA-(MV-FG) \cdot C_{re}]/FG$$

wherein in the formula, $C_{vap}$ represents the anesthetic output concentration, MV represents the inhaled gas flow, FiAA represents the inhaled gas anesthetic concentration, FG represents the fresh gas flow, and $C_{re}$ represents the re-inhaled gas anesthetic concentration.

In some embodiments of the present disclosure, when the computer program stored in the computer-readable storage medium is executed by the processor, the processor may further be specifically configured to perform the following step:

calculating the concentration of output anesthetic of the anesthetic output device based on the fresh gas flow, the inhaled gas flow, the inhaled gas anesthetic concentration, the re-inhaled gas anesthetic concentration, a predetermined change rate for the inhaled gas anesthetic concentration, and a second output concentration calculation model, thereby correspondingly obtaining an anesthetic output concentration.

The second output concentration calculation model is a model created considering an process of changes in the anesthetic concentration in the inspiratory branch. In this embodiment, a specific second output concentration calculation model is:

$$FG \cdot C_{vap}+(MV-FG) \cdot C_{re}-MV \cdot FiAA=V_{insp} \cdot \Delta FiAA;$$

wherein in the formula, FG represents the fresh gas flow, $C_{vap}$ represents the anesthetic output concentration, MV represents the inhaled gas flow, $C_{re}$ represents the re-inhaled gas anesthetic concentration, FiAA represents the inhaled gas anesthetic concentration, $V_{insp}$ represents the volume of the inspiratory branch, and $\Delta FiAA$ represents a change rate of the inhaled gas anesthetic concentration.

In some embodiments of the present disclosure, when the computer program stored in the computer-readable storage medium is executed by the processor, the processor may further be specifically configured to perform the following step:

determining whether the anesthetic output concentration is greater than a preset output concentration threshold, and if yes, triggering a corresponding abnormal response operation.

In some embodiments of the present disclosure, when the computer program stored in the computer-readable storage medium is executed by the processor, the processor may further be specifically configured to perform the following step:

calculating and displaying an anesthetic consumption rate and/or an anesthetic consumption amount in the anesthetic output device based on the anesthetic output concentration and the fresh gas flow.

It may be seen that, in this embodiment of the present disclosure, the concentration of output anesthetic of an anesthetic output device in an anesthesia machine is calculated based on fresh gas flow, inhaled gas flow, an inhaled gas anesthetic concentration, an exhaled gas anesthetic concentration, and the concentration of carbon dioxide in exhaled gas. The fresh gas flow, the inhaled gas flow, the inhaled gas anesthetic concentration, the exhaled gas anesthetic concentration, and the concentration of carbon dioxide in the exhaled gas may all be monitored based on existing sensors in a current anesthesia machine. Therefore, in this embodiment of the present disclosure, no additional hardware configuration needs to be added in a process of monitoring an anesthetic output concentration of an anesthetic output device, thereby monitoring an anesthetic output concentration at low costs.

The embodiments in the description are all described in a progressive manner, each of the embodiments focuses on the differences from the other embodiments, and reference may be made to each other for the same or similar parts among the embodiments. The apparatuses disclosed in the embodiments correspond to the methods disclosed in the embodiments and are thus described relatively simply, and reference may be made to the description of the methods for the related parts.

Those skilled in the art should be further aware that the unit and algorithm steps of the various examples described in conjunction with the embodiments disclosed herein may be implemented in electronic hardware, computer software, or a combination of both. In order to clearly illustrate hardware and software interchangeability, the compositions and steps of the various examples have been generally described in terms of function in the above description. Whether these functions are performed in hardware or software depends on the specific application and design constraints of the technical solution. Those skilled in the art could use different methods to implement the described functions for each particular application, but such implementation should not be considered to be beyond the scope of the present disclosure.

The steps of the method or algorithm described in conjunction with the embodiments disclosed herein may be implemented with hardware, a software module executed by the processor, or a combination thereof. The software module may be disposed in a random access memory (RAM), a memory, a read-only memory (ROM), an electrically programmable ROM, an electrically erasable programmable ROM, a register, a hard disk, a removable disk, CD-ROM, or any other form of storage medium known in the art.

Finally, it should be noted that the terms of relationship herein, such as first and second, are used only to distinguish one entity or operation from another entity or operation, without necessarily requiring or implying any such actual relationship or sequence between these entities or operations. Moreover, the terms "comprise," "include" or any variation thereof are intended to cover a non-exclusive inclusion, so that a process, method, article or device that comprises a series of elements not only comprises those elements but also comprises other elements not expressly listed or further comprises elements inherent to such a process, method, article, or device. In the absence of more restrictions, the element defined by the phrase "comprising a/an . . . " does not exclude the presence of a further identical element in the process, method, article or device that comprises the element.

The anesthesia machine, the anesthetic output concentration monitoring method, system, and device, and the storage medium provided in the present disclosure are described above in detail. Although the principle and implementations of the present disclosure are described by means of specific examples in the present disclosure, descriptions of the embodiments are merely intended to help understand the methods and core idea of the present disclosure. Moreover, for those skilled in the art, there may be modifications in the specific implementation and application scope based on the concept of the present disclosure. To sum up, the content of this specification should not be construed as limiting the present disclosure.

What is claimed is:

1. An anesthetic output concentration monitoring method, comprising:

monitoring, through a first sensor and a second sensor, a flow of a fresh gas flowing into a breathing circuit and a flow of an inhaled gas of an anesthetized object to obtain a fresh gas flow rate and an inhaled gas flow rate, respectively;

when the inhaled gas flow rate is greater than the fresh gas flow rate, monitoring, through a third sensor, concentrations of anesthetic in the inhaled gas and an exhaled gas of the anesthetized object to obtain an inhaled gas anesthetic concentration and an exhaled gas anesthetic concentration, respectively;

using the exhaled gas anesthetic concentration and a concentration of carbon dioxide in the exhaled gas to calculate, through a processor, a concentration of anesthetic in a gas reflowing into an inspiratory branch, in the exhaled gas, to obtain a re-inhaled gas anesthetic concentration; and using the fresh gas flow rate, the inhaled gas flow rate, the inhaled gas anesthetic concentration, and the re-inhaled gas anesthetic concentration to calculate, through the processor, a concentration of output anesthetic of an anesthetic output device to obtain an anesthetic output concentration.

2. The anesthetic output concentration monitoring method according to claim 1, wherein using the exhaled gas anesthetic concentration and the concentration of carbon dioxide in the exhaled gas to calculate the concentration of anesthetic in the gas reflowing into the inspiratory branch, in the exhaled gas, to obtain the re-inhaled gas anesthetic concentration, further comprises:

using the exhaled gas anesthetic concentration, the concentration of carbon dioxide in the exhaled gas, and a calculation model for the re-inhaled gas anesthetic concentration to calculate the concentration of anesthetic in the gas reflowing into the inspiratory branch, in the exhaled gas, to obtain the re-inhaled gas anesthetic concentration, wherein the calculation model for the re-inhaled gas anesthetic concentration is a model created based on a process of changes in a first anesthetic concentration caused by a carbon dioxide absorption canister, the first anesthetic concentration being in a gas flowing through the carbon dioxide absorption canister.

3. The anesthetic output concentration monitoring method according to claim 1, wherein using the exhaled gas anesthetic concentration and the concentration of carbon dioxide in the exhaled gas to calculate the concentration of anesthetic in the gas reflowing into the inspiratory branch, in the exhaled gas, to obtain the re-inhaled gas anesthetic concentration, further comprises:

using the exhaled gas anesthetic concentration, the concentration of carbon dioxide in the exhaled gas, and an analysis result of changes in a second anesthetic concentration of a reflowing branch to calculate the concentration of anesthetic in the gas reflowing into the inspiratory branch, in the exhaled gas, to obtain the re-inhaled gas anesthetic concentration, wherein the analysis result of changes in the second anesthetic concentration is a result obtained after an analysis of a process of changes in the second anesthetic concentration in the reflowing branch, and the reflowing branch is provided with an exhaled gas branch, a re-inhaled gas buffer device, and a carbon dioxide absorption canister.

4. The anesthetic output concentration monitoring method according to claim 3, wherein obtaining the analysis result of changes in the second anesthetic concentration of the reflowing branch further comprises:

analyzing the process of changes in the second anesthetic concentration in the reflowing branch by means of a delayer and a filter to obtain the analysis result of changes in the second anesthetic concentration.

5. The anesthetic output concentration monitoring method according to claim 3, wherein obtaining the analysis result of changes in the second anesthetic concentration further comprises:

respectively creating corresponding models for the exhaled gas branch, the re-inhaled gas buffer device, and the carbon dioxide absorption canister based on a predetermined gas delivery model that is used to characterize a relationship between an inflow gas anesthetic concentration and an outflow gas anesthetic concentration of an analysis object to obtain an anesthetic concentration analysis result comprising a first gas delivery model, a second gas delivery model, and a third gas delivery model.

6. The anesthetic output concentration monitoring method according to claim 1, further comprising: before using the exhaled gas anesthetic concentration and the concentration of carbon dioxide in the exhaled gas to calculate the concentration of anesthetic in the gas reflowing into the inspiratory branch, in the exhaled gas:

determining a calculation precision requirement of the re-inhaled gas anesthetic concentration; and determining a corresponding re-inhaled gas anesthetic concentration calculation method according to the calculation precision requirement of the re-inhaled gas anesthetic concentration.

7. The anesthetic output concentration monitoring method according to claim 6, wherein determining the calculation precision requirement of the re-inhaled gas anesthetic concentration further comprises:

obtaining branch parameters of a reflowing branch, wherein the branch parameters of the reflowing branch comprise a length or a volume of the reflowing branch or a flow of a re-inhaled gas flowing from the reflowing branch to the inspiratory branch; and determining the calculation precision requirement of the re-inhaled gas anesthetic concentration according to the branch parameters of the reflowing branch.

8. The anesthetic output concentration monitoring method according to claim 1, further comprising: after monitoring the flow of the fresh gas flowing into the breathing circuit and the flow of the inhaled gas of the anesthetized object to obtain the fresh gas flow rate and the inhaled gas flow rate, respectively:

when the inhaled gas flow rate is less than or equal to the fresh gas flow rate, monitoring the concentration of anesthetic in the inhaled gas of the anesthetized object, and determining the concentration of anesthetic as the concentration of output anesthetic of the anesthetic output device.

9. The anesthetic output concentration monitoring method according to claim 1, further comprising:

determining whether the anesthetic output concentration is greater than a preset output concentration threshold; and when determining that the anesthetic output concentration is greater than the preset output concentration threshold, triggering a corresponding abnormal response operation.

10. The anesthetic output concentration monitoring method according to claim 1, further comprising:

using the anesthetic output concentration and the fresh gas flow rate to calculate an anesthetic consumption rate or an anesthetic consumption amount in the anesthetic output device.

11. The anesthetic output concentration monitoring method according to claim 1, wherein using the fresh gas flow rate, the inhaled gas flow rate, the inhaled gas anesthetic concentration, and the re-inhaled gas anesthetic concentration to calculate the concentration of output anesthetic of the anesthetic output device to obtain the anesthetic output concentration, further comprises:

using the fresh gas flow rate, the inhaled gas flow rate, the inhaled gas anesthetic concentration, the re-inhaled gas anesthetic concentration, and a first output concentration calculation model to calculate the concentration of output anesthetic of the anesthetic output device to obtain the anesthetic output concentration, wherein the first output concentration calculation model is a model created based on a premise that a process of changes in the inhaled gas anesthetic concentration in the inspiratory branch is ignored.

12. The anesthetic output concentration monitoring method according to claim 1, wherein using the fresh gas flow rate, the inhaled gas flow rate, the inhaled gas anesthetic concentration, and the re-inhaled gas anesthetic concentration to calculate the concentration of output anesthetic of the anesthetic output device to obtain the anesthetic output concentration, further comprises:

using the fresh gas flow rate, the inhaled gas flow rate, the inhaled gas anesthetic concentration, the re-inhaled gas anesthetic concentration, a predetermined change rate for the inhaled gas anesthetic concentration, and a second output concentration calculation model to calculate the concentration of output anesthetic of the anesthetic output device to obtain the anesthetic output concentration, wherein the second output concentration calculation model is a model created based on a premise that a process of changes in the inhaled gas anesthetic concentration in the inspiratory branch is considered.

13. An anesthesia machine, comprising an anesthetic output concentration monitoring device, wherein the anesthetic output concentration monitoring device comprises a first flow sensor, a second flow sensor, an anesthetic concentration sensor, a processor, and a memory, wherein the processor is configured to execute a computer program stored in the memory to:

control the first flow sensor to monitor a flow of a fresh gas flowing into a breathing circuit to obtain a fresh gas flow rate;

control the second flow sensor to monitor a flow of an inhaled gas of an anesthetized object to obtain an inhaled gas flow rate;

when the inhaled gas flow rate is greater than the fresh gas flow rate, control the anesthetic concentration sensor to monitor concentrations of anesthetic in the inhaled gas and an exhaled gas of the anesthetized object to obtain an inhaled gas anesthetic concentration and an exhaled gas anesthetic concentration, respectively;

use the exhaled gas anesthetic concentration and a concentration of carbon dioxide in the exhaled gas to calculate a concentration of anesthetic in a gas reflowing into an inspiratory branch, in the exhaled gas, to obtain a re-inhaled gas anesthetic concentration; and use the fresh gas flow rate, the inhaled gas flow rate, the inhaled gas anesthetic concentration, and the re-inhaled gas anesthetic concentration to calculate a concentration of output anesthetic of an anesthetic output device to obtain an anesthetic output concentration.

14. The anesthesia machine according to claim 13, wherein to use the exhaled gas anesthetic concentration and the concentration of carbon dioxide in the exhaled gas to calculate the concentration of anesthetic in the gas reflowing into the inspiratory branch, in the exhaled gas, to obtain the re-inhaled gas anesthetic concentration, the processor is further configured to:

use the exhaled gas anesthetic concentration, the concentration of carbon dioxide in the exhaled gas, and a calculation model for the re-inhaled gas anesthetic concentration to calculate the concentration of anesthetic in the gas reflowing into the inspiratory branch, in the exhaled gas, to obtain the re-inhaled gas anesthetic concentration, wherein the calculation model for the re-inhaled gas anesthetic concentration is a model created based on a process of changes in a first anesthetic concentration caused by a carbon dioxide absorption canister, the first anesthetic concentration being in a gas flowing through the carbon dioxide absorption canister.

15. The anesthesia machine according to claim 13, wherein to use the exhaled gas anesthetic concentration and the concentration of carbon dioxide in the exhaled gas to calculate the concentration of anesthetic in the gas reflowing into the inspiratory branch, in the exhaled gas, to obtain the re-inhaled gas anesthetic concentration, the processor is further configured to:

use the exhaled gas anesthetic concentration, the concentration of carbon dioxide in the exhaled gas, and an analysis result of changes in a second anesthetic concentration of a reflowing branch to calculate the concentration of anesthetic in the gas reflowing into the inspiratory branch, in the exhaled gas, to obtain the re-inhaled gas anesthetic concentration, wherein the analysis result of changes in the second anesthetic concentration is a result obtained after an analysis of a process of changes in the second anesthetic concentration in the reflowing branch, and the reflowing branch is provided with an exhaled gas branch, a re-inhaled gas buffer device, and a carbon dioxide absorption canister.

16. The anesthesia machine according to claim 15, wherein to obtain the analysis result of changes in the second anesthetic concentration, the processor is further configured to:
analyze the process of changes in the second anesthetic concentration in the reflowing branch by means of a delayer and a filter to obtain the analysis result of changes in the second anesthetic concentration; or
respectively create corresponding models for the exhaled gas branch, the re-inhaled gas buffer device, and the carbon dioxide absorption canister based on a predetermined gas delivery model that is used to characterize a relationship between an inflow gas anesthetic concentration and an outflow gas anesthetic concentration of an analysis object to obtain an anesthetic concentration analysis result comprising a first gas delivery model, a second gas delivery model, and a third gas delivery model.

17. The anesthesia machine according to claim 13, before using the exhaled gas anesthetic concentration and the concentration of carbon dioxide in the exhaled gas to calculate the concentration of anesthetic in the gas reflowing into the inspiratory branch, in the exhaled gas, the processor is further configured to:
determine a calculation precision requirement of the re-inhaled gas anesthetic concentration; and
determine a corresponding re-inhaled gas anesthetic concentration calculation method according to the calculation precision requirement of the re-inhaled gas anesthetic concentration.

18. The anesthesia machine according to claim 17, wherein to determine the calculation precision requirement of the re-inhaled gas anesthetic concentration, the processor is further configured to:
obtain branch parameters of a reflowing branch, wherein the branch parameters of the reflowing branch comprise a length or a volume of the reflowing branch or a flow of a re-inhaled gas flowing from the reflowing branch to the inspiratory branch; and
determine the calculation precision requirement of the re-inhaled gas anesthetic concentration according to the branch parameters of the reflowing branch.

19. The anesthesia machine according to claim 13, after monitoring the flow of the fresh gas flowing into the breathing circuit and the flow of the inhaled gas of the anesthetized object to obtain the fresh gas flow rate and the inhaled gas flow rate, respectively, the processor is further configured to:
when the inhaled gas flow rate is less than or equal to the fresh gas flow rate, control the anesthetic concentration sensor to monitor the concentration of anesthetic in the inhaled gas of the anesthetized object, and determine the concentration of anesthetic as the concentration of output anesthetic of the anesthetic output device.

20. The anesthesia machine according to claim 13, wherein to use the fresh gas flow rate, the inhaled gas flow rate, the inhaled gas anesthetic concentration, and the re-inhaled gas anesthetic concentration to calculate the concentration of output anesthetic of the anesthetic output device to obtain the anesthetic output concentration, the processor is further configured to:
use the fresh gas flow rate, the inhaled gas flow rate, the inhaled gas anesthetic concentration, the re-inhaled gas anesthetic concentration, and a first output concentration calculation model to calculate the concentration of output anesthetic of the anesthetic output device to obtain the anesthetic output concentration, wherein the first output concentration calculation model is a model created based on a premise that a process of changes in the inhaled gas anesthetic concentration in the inspiratory branch is ignored; or
use the fresh gas flow rate, the inhaled gas flow rate, the inhaled gas anesthetic concentration, the re-inhaled gas anesthetic concentration, a predetermined change rate for the inhaled gas anesthetic concentration, and a second output concentration calculation model to calculate the concentration of output anesthetic of the anesthetic output device to obtain the anesthetic output concentration, wherein the second output concentration calculation model is a model created based on a premise that a process of changes in the inhaled gas anesthetic concentration in the inspiratory branch is considered.

* * * * *